United States Patent [19]

St. George et al.

[11] Patent Number: 5,900,499

[45] Date of Patent: May 4, 1999

[54] PREPARATION OF AMINOPOLYCARBOXYLATE-FERRIC SOLUTIONS WITH IMPROVED LONG-TERM STABILITY

[75] Inventors: George M. St. George, Lake Jackson; David A. Wilson, Richwood, both of Tex.

[73] Assignee: The Dow Chemical Company, Midland, Mich.

[21] Appl. No.: 08/889,270

[22] Filed: Jul. 8, 1997

[51] Int. Cl.$^6$ ...................................................... C07F 15/02
[52] U.S. Cl. ............................................................. 556/148
[58] Field of Search ............................................. 556/148

[56] References Cited

U.S. PATENT DOCUMENTS

| | | | |
|---|---|---|---|
| 3,767,689 | 10/1973 | Donovan et al. ...................... | 260/439 |
| 3,867,419 | 2/1975 | Iwano et al. ............................ | 260/439 |
| 4,364,871 | 12/1982 | Svatek et al. .......................... | 260/439 |
| 4,438,040 | 3/1984 | Svatek et al. .......................... | 260/439 |
| 5,077,037 | 12/1991 | Wallace ...................................... | 424/9 |
| 5,110,965 | 5/1992 | Thunberg et al. ..................... | 556/148 |

FOREIGN PATENT DOCUMENTS 0 694 528 A2   1/1996   European Pat. Off. .

*Primary Examiner*—Porfirio Nazario-Gonzalez

[57] ABSTRACT

A process for producing a ferric aminopolycarboxylic acid chelate with improved long term stability is disclosed. The process involves heating a mixture of iron oxide, ammonia and aminopolycarboxylic acid chelant at an elevated temperature for a sufficient time to improve the stability of the formed chelate.

12 Claims, No Drawings

PREPARATION OF AMINOPOLYCARBOXYLATE-FERRIC SOLUTIONS WITH IMPROVED LONG-TERM STABILITY

BACKGROUND OF THE INVENTION

The present invention is to a process for producing ferric-aminopolycarboxylic acid chelates with improved long term stability.

In the photographic industry, the oxidation of metallic silver in photographic images or negatives to silver ion is known as bleaching. A desirable bleaching agent will react rapidly with silver and then react rapidly with air to regenerate the bleaching agent. Ferric compounds have been used for this purpose for decades. The ferric compound in the most widespread use today is ferric ammonium ethylenediaminetetraacetate because of its desirable redox properties and ease of preparation from inexpensive commercial chemicals such as, ferrosoferric oxide, ethylenediaminetetraacetic acid (EDTA) and ammonia.

Donovan and Surash, U.S. Pat. No. 3,767,689, and Svatek, et al. U.S. Pat. Nos. 4,364,871, and 4,438,040, describe the formation of ferric-aminopolycarboxylic acid chelates by the reaction of iron oxide with ammoniated EDTA in an aqueous mixture at temperatures up to 105° C. for less than three hours, followed by pH adjustment, aeration, and filtration to give a ferric ammonium EDTA solution suitable for bleaching. A more recent variation of the method, described by Thunberg, et al. (U.S. Pat. No. 5,110,965), involves the use of ferrous salts to catalyze the reaction between the iron oxide and ammoniated EDTA.

Whereas chelate solutions made by the aforementioned processes are useful for photographic bleaching, over time they deposit fine, black, particulate matter which would be detrimental to the quality of photographs prepared using said solutions. It would be desirable, therefore, to produce ferric ammonium EDTA solutions which are more stable against the formation of the dark particulates.

SUMMARY OF THE INVENTION

The present invention is to a process for producing a ferric ammonium chelate of an aminopolycarboxylic acid with improved long term stability wherein an oxide of iron is reacted with an aminopolycarboxylic acid chelant in the presence of a base, which comprises: (1) providing a mixture in water of ammonia together with the chelant in a molar ratio of ammonia to chelant of about 0.5 to about 1.8, (2) adding to the mixture the oxide of iron at less than 1 mole of iron per mole of chelant, (3) heating the mixture for a sufficient time and temperature to produce a chelate which is stable for at least 28 days against the formation of fine precipitates as measured when the final chelate is stored at 40° C., (4) cooling the mixture to a temperature below about 75° C., (5) introducing ammonia to said mixture in sufficient amount to dissolve and to maintain in solution the iron chelate so formed, (6) oxidizing any ferrous ion present in the chelate solution to the ferric ion and (7) filtering the chelate solution.

In one particular embodiment of the new process, ammoniated EDTA slurry is reacted with ferrosoferric oxide at reflux temperature (105–110° C.) for in excess of three hours, followed by the cooling, addition of ammonia and aeration steps as above.

In a second specific embodiment of the process, ferrosoferric oxide and ammoniated EDTA slurry are reacted in a closed system (e.g., an autoclave) at temperatures exceeding 115° C. for 10 to 75 minutes, followed by cooling, addition of ammonia and aeration steps as above.

The methods of the present invention promote the production of ferric ammonium EDTA solutions with significantly improved stability against dark particulate formation as compared with solutions prepared by the methods disclosed in the art.

DETAILED DESCRIPTION OF THE INVENTION

It has been found that solutions of ferric ammonium aminopolycarboxylic acids with superior stability can be prepared from ferrosoferric oxide, aminopolycarboxylic acid and ammonia under the conditions disclosed herein.

Aminopolycarboxylic acids that are useful in the present invention as the chelant moiety are those which are capable of chelating iron. Examples of such chelants include nitrilotriacetic acid (NTA); iminodiacetic acid (IDA) and N-substituted derivatives thereof; 1,3-propanediaminetetraacetic acid (1,3-PDTA); ethylenediaminetetraacetic acid; N-hydroxyethylethylenediaminetriacetic acid (HEDTA) and diethylenetriaminepentaacetic acid (DTPA). Chelants containing one or more succinic acid moieties, such as ethylenediaminedisuccinic acid, can also be used as chelants in the current process. Preferred chelants are NTA, 1,3-PDTA, HEDTA, DTPA and EDTA. More preferably the chelant is EDTA.

In one specific embodiment of the present invention, ferrosoferric oxide, EDTA, and ammonia are combined in water so that the EDTA:iron mole ratio is between about 1.0 and about 1.8. Preferably the EDTA:iron mole ratio is between about 1.0 and about 1.5. More preferably, the EDTA:iron mole ratio is between about 1.1 and about 1.4. The ammonia:EDTA mole ratio generally is initially between about 0.5 and about 1.8. Preferably the ammonia:EDTA mole ratio is initially between about 1.0 and about 1.5. More preferably the ammonia:EDTA mole ratio is initially between about 1.2 and about 1.4. The amount of water added is chosen so that the concentration of iron in the final mixture is from about 4 to about 8 percent by weight.

The mixture of ammonia, EDTA and iron is then heated to boiling (ca. 105–110° C.) and kept there for three to eight hours, preferably three to six hours. More preferably the mixture is heated at boiling for four to six hours. During this time, water is added periodically to replace evaporative losses. The resulting mixture is then cooled to 25–65° C., preferably 30–50° C. More preferably the resulting mixtures is cooled to 35–50° C. Cold aqueous ammonia is then added to give a solution of desirable pH, generally between 7 and 8. The temperature of the mixture at this stage is generally kept below 60° C. The solution is then oxidized by air sparging until there is little or no detectable amount of ferrous iron remaining. After filtration through a fine (ca. 0.5 micron) filter, the resulting solution has improved stability against the formation of dark particulates as compared to such solutions prepared by processes known in the art.

In another preferred embodiment of the invention, an autoclave is charged with ferrosoferric oxide, EDTA, ammonia, and water as above. The autoclave is sealed; and, with vigorous stirring, the temperature is raised to 115–150° C., preferably 115–140° C., and more preferably 115–125° C. The length of time of the reaction is dependent on the temperature and is generally from about 10 to about 75 minutes and preferably from about 15 to about 60 minutes.

For example, a time of about one hour is appropriate for a temperature of 115° C. and about fifteen minutes for a temperature of 150° C. The autoclave is then cooled as above, and the pressure is vented. The mixture is ammoniated, aerated, and filtered as above, providing a solution with improved stability against the formation of dark particulates as compared to such solutions prepared by processes known in the art.

Increased stability against the formation of dark particulates is conveniently measured by storing the chelate solutions at 40° C. and observing the formation of precipitate with time by filtering a sample of the stored chelate solution (s) through a 0.45 micron filter.

While specific embodiments have been demonstrated using EDTA as the chelant, other aminocarboxylates may be substituted for EDTA.

Certain modifications of the embodiments above will be apparent to one skilled in the art and are not considered out of the scope of this invention. For example, the ammoniation that follows the chelation reaction can be performed using anhydrous ammonia in place of aqueous ammonia. Furthermore, any reactor capable of withstanding the pressure and temperature of the second embodiment can be used in place of the autoclave.

During the course of the reactions of the present invention, a certain amount of EDTA is destroyed. Extended heating of the reaction mixtures exacerbates this situation. Whereas it is obvious that such extended heating may be performed if greater amounts of EDTA are used, the charges and conditions described above provide chelate solutions of superior stability while minimizing EDTA losses.

The invention will be further clarified by a consideration of the following examples, which are intended to be purely exemplary of the present invention.

Stability Test:

Immediately after preparation, the product solution is stored in a high-density, polyethylene bottle in a constant-temperature oven at 40° C. At appropriate intervals (usually weekly), a 125-ml sample of the solution is diluted with 125 ml of deionized water; and the resulting solution is passed through a 0.45-micron cellulose acetate filter (25-mm diameter). Failure (loss of solution stability) is recognized when the diluted solution leaves a black residue on the filter.

EXAMPLE 1

Two 2-liter beakers were each charged with EDTA acid (747 g, 2.56 moles); deionized water (750 g); 28% aqueous ammonia (195 g, 3.21 moles); and $Fe_3O_4$ (171 g, 2.22 moles Fe). With vigorous stirring, the temperature was raised to the boiling point (108° C.) over the course of 20 min. and maintained there for six hours. (Deionized water was added occasionally to replace that which was lost to evaporation.) The resulting solutions were combined in one 4-liter beaker and allowed to cool to 48° C. (over the course of one hour). Ice-cold, 28% ammonia (280 g, 4.60 moles) was added slowly, keeping the temperature of the solution below 55° C. The solution was sparged with air overnight, then filtered through a 0.45-micron nylon filter. 3258 g of filtered solution was obtained. Analytical data are given in Table 1.

EXAMPLE 2

A 2-liter, stainless-steel autoclave was charged with EDTA acid (727 g, 2.49 moles); deionized water (600 g); 28% ammonia (195 g, 3.21 moles); and $Fe_3O_4$ (171 g, 2.22 moles Fe). With vigorous stirring, the mixture was heated to 120° C. over the course of 25 min. and maintained there for 45 min. (The final pressure in the autoclave was ca. 100 psig.) The mixture was cooled to 35° C. over the course of 10 min. Pressure was vented from the autoclave, which was then opened. The product mixture was transferred to a 2-liter beaker; and 28% ammonia (140 g, 2.30 moles) was added, causing a temperature rise to 49° C. The solution was sparged with air overnight, then filtered through a 0.45-micron nylon filter; 1691 g of product was obtained. Analytical data are given in Table 1.

COMPARATIVE EXAMPLE A

A 2-liter beaker was charged with deionized water (600 g); $Fe_3O_4$ (171 g, 2.22 moles Fe); 28% ammonia (67.5 g, 1.11 mole); and EDTA acid (700 g, 2.40 moles). With vigorous stirring, the thick slurry was heated to 65° C. over the course of 15 min.; and $FeSO_4 \cdot 7H_2O$ (6.1 g, 0.022 mole) was added. After a brief exotherm to 70° C., the temperature returned to 65° C. and was kept there for six hours. The solution was then cooled to 35° C. over the course of 50 min. Ice-cold 28% ammonia (204 g, 3.35 moles) was added, causing a rise in temperature to 55° C. The solution was sparged with air overnight; and then additional 28% ammonia (21 g, 0.35 mole) was added. The resulting solution was filtered through a 0.45-micron nylon filter, giving 1738 g of product. Analytical data are given in Table 1.

COMPARATIVE EXAMPLE B

A 2-liter beaker was charged with EDTA acid (485 g, 1.66 mole); deionized water (500 g); 28% ammonia (130 g, 2.14 moles); and $Fe_3O_4$ (114 g, 1.48 mole Fe). With vigorous stirring, the temperature was raised to 90° C. over the course of 30 min. and maintained there for another 30 min. The mixture was cooled to 60° C. over the course of 25 min.; and 28% ammonia (90 g, 1.48 mole) was added slowly. The solution was air-sparged for 210 min. and then filtered through a 0.45-micron nylon filter, giving 1180 g product. Analytical data are given in Table 1.

TABLE 1

| Solution | Assay[a] | Days to Failure[b] |
|---|---|---|
| Example 1 | 49.30 | 53 |
| Example 2 | 49.16 | >56 |
| Comp. Ex. A | 49.04 | 18 |
| Comp. Ex. B | 48.43 | 20 |

[a]weight percent of solution as $(NH_4)FeEDTA \cdot NH_4OH$
[b]days at 40° C. until the stability test showed black precipitate Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A process for producing a ferric ammonium chelate of an aminopolycarboxylic acid wherein an oxide of iron is reacted with an aminopolycarboxylic acid chelant in the presence of a base, which comprises: (1) providing a mixture in water of ammonia together with the chelant in a molar ratio of ammonia to chelant of about 0.5 to about 1.8, (2) adding to the mixture the oxide of iron at less than 1 mole of iron per mole of chelant, (3) heating the mixture for a sufficient time and temperature to produce a chelate which is stable for at least 28 days against the formation of fine precipitates as measured when the final chelate is stored at 40° C., (4) cooling the mixture to a temperature below about 75° C., (5) introducing ammonia to said mixture in sufficient amount to dissolve and to maintain in solution the iron chelate so formed, (6) oxidizing any ferrous ion present in the chelate solution to the ferric ion and (7) filtering the chelate solution.

2. The process of claim 1 wherein the mixture in step (3) is heated at reflux temperature for 3 or more hours.

3. The process of claim 2 wherein the reflux temperature is greater than 105° C.

4. The process of claim 1 wherein the mixture in step (3) is heated for about 10 to about 75 minutes at a temperature of greater than 115° C.

5. The process of claim 1 wherein the aminopolycarboxylic acid is nitrilotriacetic acid, 1,3-propanediaminetetraacetic acid, ethylenediaminetetraacetic acid, N-hydroxyethylethylenediaminetriaacetic acid, diethylenetriaminepentaacetic acid, iminodiacetic acid (IDA) and N-substituted derivatives thereof or ethylenediaminedisuccinic acid.

6. The process of claim 5 wherein the aminopolycarboxylic acid is nitrilotriacetic acid, 1,3-propanediaminetetraacetic acid, ethylenediaminetetraacetic acid, N-hydroxyethylethylenediaminetriaacetic acid or diethylenetriaminepentaacetic acid.

7. The process of claim 6 wherein the aminopolycarboxylic acid is ethylenediaminetetraacetic acid.

8. The process of claim 1 wherein the mole ratio of ammonia to chelant in step (1) is from about 1.2 to about 1.3.

9. The process of claim 1 wherein the oxide of iron in step (2) is added at a molar ratio of from about 0.8 to about 0.96 mole iron per mole of chelant.

10. The process of claim 1 wherein the oxidation of step (6) is accomplished by contacting with an oxygen-containing gas.

11. The process of claim 10 wherein the oxygen-containing gas is air.

12. The process of claim 2 wherein the oxide of iron is $Fe_3O_4$.

* * * * *